US007012692B2

(12) United States Patent
Yamaguchi et al.

(10) Patent No.: US 7,012,692 B2
(45) Date of Patent: Mar. 14, 2006

(54) PHOTOTHERMAL CONVERSION SPECTROSCOPIC ANALYSIS METHOD, AND PHOTOTHERMAL CONVERSION SPECTROSCOPIC ANALYSIS APPARATUS FOR CARRYING OUT THE METHOD

(75) Inventors: Jun Yamaguchi, Tokyo (JP); Akihiko Hattori, Osaka (JP); Takehiko Kitamori, Tokyo (JP); Manabu Tokeshi, Kanagawa (JP)

(73) Assignees: Nippon Sheet Glass Co., Ltd., Osaka (JP); Kanagawa Academy of Science & Technology, Kawasaki (JP)

( * ) Notice: Subject to any disclaimer, the term of this patent is extended or adjusted under 35 U.S.C. 154(b) by 47 days.

(21) Appl. No.: 10/734,980

(22) Filed: Dec. 12, 2003

(65) Prior Publication Data

US 2004/0233450 A1    Nov. 25, 2004

Related U.S. Application Data

(63) Continuation of application No. PCT/JP02/05694, filed on Jun. 7, 2002.

(30) Foreign Application Priority Data

Jun. 13, 2001  (JP) .............................. 2001-178819

(51) Int. Cl.
    *G01N 21/01* (2006.01)
(52) U.S. Cl. ..................................... 356/432; 250/344
(58) Field of Classification Search ........ 356/432–436, 356/445–448, 128, 317–318, 422; 250/343–344, 250/347, 352, 437
    See application file for complete search history.

(56) References Cited

U.S. PATENT DOCUMENTS

| 4,243,327 | A | * | 1/1981 | Frosch et al. ............... 356/432 |
| 4,310,762 | A | * | 1/1982 | Harris et al. ................ 250/343 |
| 4,521,118 | A | * | 6/1985 | Rosencwaig ................... 374/5 |
| 4,938,593 | A | * | 7/1990 | Morris et al. ............... 356/344 |
| 4,974,089 | A | * | 11/1990 | Gilligan ................... 348/217.1 |
| 5,001,718 | A | * | 3/1991 | Burrows et al. ............. 372/33 |
| 5,253,102 | A | * | 10/1993 | Okazaki ..................... 359/328 |
| 5,557,407 | A | * | 9/1996 | Takamiya et al. ........... 356/499 |
| 5,796,517 | A | * | 8/1998 | Sensui et al. ............... 359/426 |

FOREIGN PATENT DOCUMENTS

| JP | 61-255308 A | | 11/1986 |
| JP | 10142177 A | * | 5/1998 |
| JP | 2000-2677 A | | 1/2000 |

* cited by examiner

*Primary Examiner*—Gregory J. Toatley, Jr.
*Assistant Examiner*—Sang H. Nguyen
(74) *Attorney, Agent, or Firm*—Frishauf, Holtz, Goodman & Chick, P.C.

(57) ABSTRACT

It is an object to provide a photothermal conversion spectroscopic analysis method that enables measurement to be carried out with high sensitivity, and a photothermal conversion spectroscopic analysis apparatus that carries out the method. The photothermal conversion spectroscopic analysis apparatus is comprised of an exciting light source 111, a chopper 112 that is disposed close to the exciting light source 111 in the optical path of exciting light emitted from the exciting light source 111, a mirror 114 that changes the direction of travel of the exciting light, a detecting light source 120, a dichroic mirror 113 that has detecting light from the detecting light source 120 incident thereon and makes the exciting light and the detecting light coaxial, a lens 10 that has a suitable amount of chromatic aberration, and a holder 15 that holds the lens 10 such as to enable adjustment along three axes.

8 Claims, 6 Drawing Sheets

PHOTOTHERMAL CONVERSION SPECTROSCOPIC ANALYSIS METHOD, AND PHOTOTHERMAL CONVERSION SPECTROSCOPIC ANALYSIS APPARATUS FOR CARRYING OUT THE METHOD

This application is a Continuation Application of International Application PCT/JP02/05694 filed Jun. 7, 2002.

TECHNICAL FIELD

The present invention relates to a photothermal conversion spectroscopic analysis method and apparatus according to which exciting light is convergently irradiated onto a sample to form a thermal lens, and detecting light is also irradiated onto the sample, and detecting light that has passed through the sample is received, whereby a change in intensity of the detecting light caused by refraction due to the thermal lens is measured, and in particular relates to a photothermal conversion spectroscopic analysis method and apparatus that enable high-precision ultramicroanalysis to be carried out through measurement in a very small space, and moreover enable measurement to be carried out easily in any chosen location.

BACKGROUND ART

In recent years, spectroscopic analysis has come to be widely used as a method for carrying out analysis or measurement on semiconductors, biological samples, various types of liquid sample, and so on. However, with a conventional spectroscopic analysis method, in the case of analyzing a very small amount of a substance or a very small sample in a very small space, it has been necessary to carry out the measurement in a vacuum environment. Moreover, there has been a problem that the sample may be damaged or destroyed upon using an electron beam or ion beam.

Moreover, when handling an extremely small amount of a sample in a solution, biological tissue, or the like, it is essential to use an optical microscope that enables analysis to be carried out with high precision and high spatial resolution. The only type of such microscope actually used is a laser fluorescence microscope. The target of analysis is thus naturally limited to being a molecule that is fluorescent with a laser fluorescence microscope.

Due to this state of affairs, there have been demands for an analysis method according to which a vacuum environment is not required, analysis can be carried out without contacting or risking damaging the sample, and moreover the target of analysis is not limited to being a fluorescent molecule, and analysis can be carried out with high precision and high spatial resolution.

A photothermal conversion spectroscopic analysis method that uses a thermal lens effect brought about by photothermal conversion is attracting attention as an analysis method that satisfies these demands.

This photothermal conversion spectroscopic analysis method uses a photothermal conversion effect in which light is convergently irradiated onto a sample, whereupon a solute in the sample absorbs the light, and hence the temperature of the solvent is locally raised by thermal energy released due to the absorbed light, whereby the refractive index changes, and hence a thermal lens is formed.

FIG. 3 is a view useful in explaining the principle of a thermal lens.

In FIG. 3, exciting light is convergently irradiated onto an extremely small sample via an objective lens of a microscope, whereby a photothermal conversion effect is brought about. For most substances, the refractive index drops as the temperature rises. Consequently, in the sample onto which the exciting light has been convergently irradiated, the refractive index drops, with the drop in the refractive index being larger closer to the center of the converged light, which is where the extent of the rise in temperature is largest; moving away from the center of the converged light toward the periphery, the extent of the rise in temperature becomes smaller due to thermal diffusion, and hence the drop in refractive index becomes smaller. Optically, the resulting refractive index distribution produces exactly the same effect as a concave lens, and hence the effect is referred to as the thermal lens effect. The size of the thermal lens effect, i.e. the power of the concave lens, is proportional to the optical absorbance of the sample. Moreover, in the case that the refractive index increases with temperature, a similar effect is produced, but conversely the thermal lens is convex.

In the photothermal conversion spectroscopic analysis method described above, thermal diffusion in the sample, i.e. change in the refractive index of the sample, is observed, and hence the method is suitable for detecting concentrations in extremely small samples.

A photothermal conversion spectroscopic analysis apparatus that carries out the photothermal conversion spectroscopic analysis method described above is described, for example, in Japanese Laid-open Patent Publication (Kokai) No. 10-232210.

In such a photothermal conversion spectroscopic analysis apparatus, the sample is disposed below the objective lens of a microscope, and exciting light of a predetermined wavelength outputted from an exciting light source is introduced into the microscope, and thus convergently irradiated via the objective lens onto an extremely small region in the sample. A thermal lens is thus formed centered on the focal position of the convergently irradiated exciting light.

Moreover, detecting light having a wavelength different to that of the exciting light is emitted from a detecting light source, and is introduced into the microscope, before exiting from the microscope. The detecting light that has exited from the microscope is convergently irradiated onto the thermal lens that has been formed in the sample by the exciting light. Upon passing through the sample, the detecting light is diverged or converged by the effect of the thermal lens. The diverged or converged detecting light exiting from the sample is taken as signal light, and passes through a converging lens and a filter, or just a filter, before being received by a detector and thus detected. The intensity of the detected signal light depends on the refractive index of the thermal lens formed in the sample.

The frequency of the detecting light may be the same as that of the exciting light, or the exciting light may also be used as the detecting light. In general, good sensitivity is obtained in the case that the exciting light and the detecting light are made to have different frequencies to one another.

However, with a photothermal conversion spectroscopic analysis apparatus as described above, the structure of the optical system and so on for the light sources, the measurement section and the detection section (photoelectric conversion section) is complex, and hence such an apparatus has been large in size and has thus lacked portability. Consequently, there is a problem in that when carrying out analysis or a chemical reaction using such a photothermal conversion spectroscopic analysis apparatus, there are limitations with regard to the installation site of the apparatus and the operation of the apparatus, and hence there is a problem of the work efficiency for a user being poor.

In many cases of using a photothermal conversion spectroscopic analysis method that makes use of a thermal lens, it is necessary for the focal position of the exciting light and the focal position of the detecting light to be different to one another. FIGS. 4A and 4B are views useful in explaining the formation position of a thermal lens and the focal position of detecting light in the direction of travel of exciting light; FIG. 4A shows a case in which an objective lens has chromatic aberration, and FIG. 4B shows a case in which the objective lens does not have chromatic aberration.

In the case that the objective lens 130 has chromatic aberration, as shown in FIG. 4A, the thermal lens 131 is formed at the focal position 132 of the exciting light, and the focal position 133 of the detecting light is shifted by an amount ΔL from the focal position 132 of the exciting light; changes in the refractive index of the thermal lens 131 can thus be detected as changes in the focal distance of the detecting light. On the other hand, in the case that the objective lens 130 does not have chromatic aberration, as shown in FIG. 4B, the focal position 133 of the detecting light is almost exactly the same as the focal position 132 of the exciting light, i.e. the position of the thermal lens 131. As a result, the detecting light is not refracted by the thermal lens 131, and hence changes in the refractive index of the thermal lens 131 cannot be detected.

However, the objective lens of a microscope is generally manufactured so as not to have chromatic aberration, and hence for the reason described above, the focal position 133 of the detecting light is almost exactly the same as the position of the thermal lens 131 formed at the focal position 132 of the exciting light (FIG. 4B). Changes in the refractive index of the thermal lens 131 thus cannot be detected. There is thus a problem in that the position of the sample where the thermal lens is formed must be shifted from the focal position 133 of the detecting light every time measurement is carried out as shown in FIG. 5A or 5B, to, for example, shift a focal position of the detecting light to a position 134 as shown in FIG. 5A. Alternatively, the detecting light must be diverged or converged slightly using a lens (not shown) before being introduced into the objective lens 130 so that the focal position 133 of the detecting light is shifted from the thermal lens 131 as shown in FIG. 6. This requires time and effort, and hence the work efficiency for a user is poor.

It is an object of the present invention to provide a photothermal conversion spectroscopic analysis method that enables measurement to be carried out with high sensitivity, and a small-sized photothermal conversion spectroscopic analysis apparatus that carries out the method.

DISCLOSURE OF THE INVENTION

To attain the above object, in a first aspect of the present invention, there is provided a photothermal conversion spectroscopic analysis method having a convergent irradiation step of convergently irradiating exciting light and detecting light onto a sample using a converging lens, and a measurement step of measuring a change in intensity accompanying deflection of the detecting light upon passing through a thermal lens produced through the convergent irradiation of the exciting light, characterized in that the exciting light and the detecting light convergently irradiated in the convergent irradiation step have different frequencies to one another, and the converging lens satisfies a condition that a length of a shift in a focal position of the detecting light from a focal position of the exciting light is in a range of 2 times to 30 times a confocal length at the frequency of the exciting light.

To attain the above object, in a second aspect of the present invention, there is provided a photothermal conversion spectroscopic analysis method having a convergent irradiation step of convergently irradiating exciting light and detecting light onto a sample using a converging lens, and a measurement step of measuring a change in intensity accompanying deflection of the detecting light upon passing through a thermal lens produced through the convergent irradiation of the exciting light, characterized in that the exciting light and the detecting light have different frequencies to one another, and the converging lens satisfies a condition that a shift in a focal position of the detecting light relative to a focal position of the exciting light is in a range of 2 times to 25 times a confocal length at the frequency of the exciting light.

In the first and second aspects of the present invention, the converging lens is preferably a rod lens.

To attain the above object, in a third aspect of the present invention, there is provided a photothermal conversion spectroscopic analysis apparatus comprising a converging lens for convergently irradiating exciting light and detecting light onto a sample, and measurement means for measuring a change in intensity accompanying deflection of the detecting light upon passing through a thermal lens produced through the convergent irradiation of the exciting light, characterized in that the convergently irradiated exciting light and detecting light have different frequencies to one another, and the converging lens satisfies a condition that a length of a shift in a focal position of the detecting light from a focal position of the exciting light is in a range of 2 times to 30 times a confocal length at the frequency of the exciting light.

To attain the above object, in a fourth aspect of the present invention, there is provided a photothermal conversion spectroscopic analysis apparatus comprising a converging lens for convergently irradiating exciting light and detecting light onto a sample, and measurement means for measuring a change in intensity accompanying deflection of the detecting light upon passing through a thermal lens produced through the convergent irradiation of the exciting light, characterized in that the convergently irradiated exciting light and detecting light have different frequencies to one another, and the converging lens satisfies a condition that a length of a shift in a focal position of the detecting light from a focal position of the exciting light is in a range of 2 times to 25 times a confocal length at the frequency of the exciting light.

In the third and fourth aspects of the present invention, the converging lens is preferably a rod lens.

BEST MODE FOR CARRYING OUT THE INVENTION

A photothermal conversion spectroscopic analysis method, and a photothermal conversion spectroscopic analysis apparatus that carries out the method, according to an embodiment of the present invention will now be described in detail with reference to the drawings.

Figure 1:
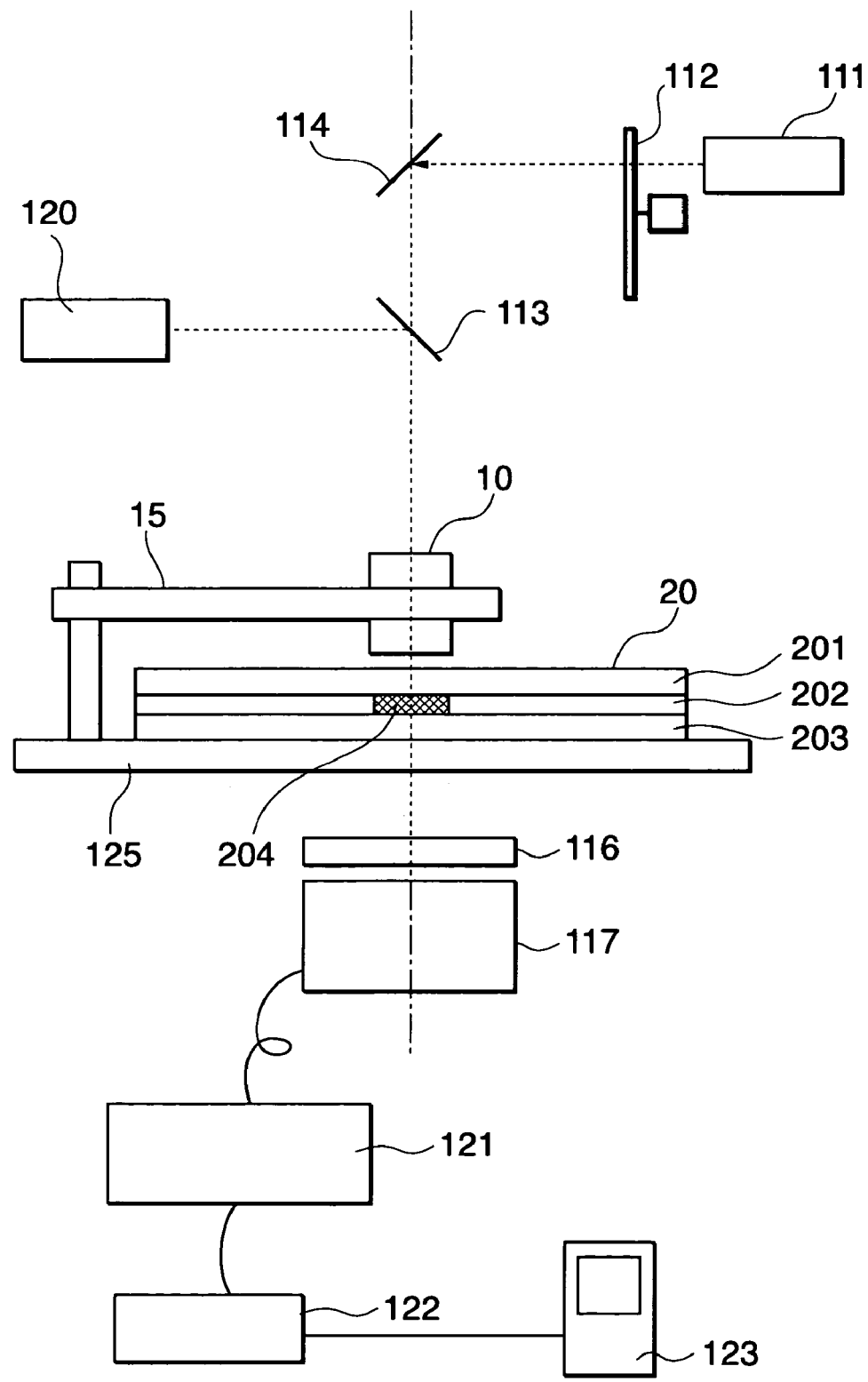
FIG. 1 is a view schematically showing the construction of a photothermal conversion spectroscopic analysis apparatus according to an embodiment of the present invention.

FIG. 1 is a view schematically showing the construction of a photothermal conversion spectroscopic analysis apparatus according to an embodiment of the present invention.

In FIG. 1, a chopper 112 for modulating exciting light to improve the S/N ratio of a thermal lens signal, described later, is disposed close to an exciting light source 111 in the optical path of the exciting light, which is emitted from the exciting light source 111. The modulated exciting light has its direction of travel changed by a mirror 114, and then passes through a dichroic mirror 113. Out of the two faces of the dichroic mirror 113, detecting light from a detecting light source 120 is made to be incident on the face on the opposite side to the face on which the exciting light is incident. The detecting light is reflected by the dichroic mirror 113, thus becoming coaxial with the exciting light, and then the exciting light and the detecting light are led to a lens 10 having a suitable amount of chromatic aberration.

The lens 10 is held by a movable holder 15. In the present embodiment, the lens 10 is a gradient index rod lens. Note, however, that so long as the lens 10 has a predetermined amount of chromatic aberration, the lens 10 is not limited to a gradient index rod lens.

The rod lens 10 is comprised of a transparent cylindrical body made, for example, of glass or plastic, wherein the refractive index changes continuously from the center toward the periphery (see, for example, Japanese Examined Patent Application Publication (Kokoku) No. 63-63502).

Such a rod lens 10 is known as a converging light-transmitting body for which the refractive index n(r) at a position a distance r from the central axis in the radial direction is given approximately by the quadratic equation in r, $$n(r) = n_0 \{1 - (g^2/2) r^2\},$$

wherein $n_0$ represents the refractive index at the central axis, and g represents a quadratic distribution constant.

If the length $z_0$ of the rod lens 10 is chosen to be in a range of $0 < z_0 < \pi/2\,g$, then even though the rod lens 10 has flat end faces, the image formation characteristics of the rod lens 10 will be the same as those of an ordinary convex lens; when a parallel light beam is incident on the rod lens 10, a focal point will be formed at a position a distance $s_0$ from the end of the rod lens 10 from which the light beam exits, where $$s_0 = \cot(gz_0)/n_0 g.$$

The rod lens 10 may be manufactured, for example, using the following method.

A rod is first formed from a glass having as principal components thereof 57 to 63 mol % of $SiO_2$, 17 to 23 mol % of $B_2O_3$, 5 to 17 mol % of $Na_2O$, and 3 to 15 mol % of $Tl_2O$, and then the glass rod is treated in an ion exchange medium such as a potassium nitrate bath, thus carrying out ion exchange between thallium ions and sodium ions in the glass and potassium ions in the medium, to give a refractive index distribution in the glass rod in which the refractive index decreases continuously from the center of the glass rod toward the periphery of the glass rod.

Because the optical axis of the cylindrical rod lens 10 intersects the two end faces of the rod lens 10 at right angles, the optical axis of the exciting light and the detecting light can easily be aligned with the optical axis of the rod lens 10. Furthermore, the rod lens 10 is considerably smaller in size than a microscope objective lens, and hence the apparatus as a whole can be made smaller in size.

Below the rod lens 10, a channel-formed plate-shaped member 20 through which a sample to be subjected to detection is made to flow is provided on an X-Y sample stage 125. The X-Y sample stage 125 can be moved on a plane orthogonal to the plane of the paper in FIG. 1.

The channel-formed plate-shaped member 20 through which the sample to be subjected to detection is made to flow is comprised of three glass substrates 201, 202 and 203 bonded on top of one another; a channel 204 for carrying out mixing, agitation, synthesis, separation, extraction, detection or the like on the sample is formed in the middle glass substrate 202.

From the perspective of durability and chemical resistance, the channel-formed plate-shaped member 20 is preferably made of a glass. In particular, envisaging usage with biological samples such as cell samples, for example for DNA analysis, it is preferable to use a glass having high acid resistance and alkali resistance, specifically a borosilicate glass, a soda lime glass, an aluminoborosilicate glass, a quartz glass or the like. However, if the usage is limited accordingly, then a channel-formed plate-shaped member 20 made of an organic substance such as a plastic can be used instead.

The focal position of the exciting light focussed by the rod lens 10 must be within the channel 204 of the channel-formed plate-shaped member 20. However, the rod lens 10 does not have to be in contact with the channel-formed plate-shaped member 20. In the case that the rod lens 10 is made to be in contact with the channel-formed plate-shaped member 20, the focal position of the rod lens 10 can be adjusted through the thickness of the upper glass substrate 201 of the channel-formed plate-shaped member 20. In the case that the thickness of the upper glass substrate 201 is insufficient, a spacer for adjusting the focal position may be inserted between the rod lens 10 and the upper glass substrate 201. In these cases, subsequent adjustment of the focal position becomes unnecessary, and hence the apparatus can be made yet smaller in size.

A description will be now given regarding what should be the size of the shift (ΔL) between the focal position of the exciting light and the focal position of the detecting light. In the case that the target of measurement is an extremely thin film, a result has been obtained that $\sqrt{3}$ times the confocal length of the objective lens used to convergently irradiate the exciting light is optimum (Analyst, August 1995, Vol. 120, 2053). The confocal length Ic (nm) is given by $Ic=\pi \times (d/2)^2/\lambda_1$. Here, d represents the Airy disk and is given by $d=1.22 \times \lambda_1/NA$, $\lambda_1$ represents the wavelength (nm) of the exciting light, and NA represents the numerical aperture of the rod lens 10 used. The value of ΔL represents the difference between the focal position of the exciting light and the focal position of the detecting light; there is no distinction according to whether the focal distance of the detecting light is longer or shorter than the focal distance of the exciting light.

However, the above optimum value for ΔL is only for the case that the exciting light and the detecting light have the same frequency, and the thickness of the sample does not exceed the confocal length of the objective lens.

At present, integration technology for carrying out chemical reactions in very small spaces is attracting attention from the perspective of the rapidity of chemical reactions, and carrying out reactions using very small amounts, on-site analysis and so on, and research is being carried out with vigor throughout the world.

As one example of such integration technology, there are apparatuses that aim to carry out any of mixing, reaction, separation, extraction, and detection on a sample in a very fine channel formed in a small glass substrate or the like. Such an apparatus may be used with a single function, for example for only separation, or may be used with a combination of functions.

As an example of an apparatus for only separation, an electrophoresis apparatus for analyzing extremely small amounts of proteins, nucleic acids or the like has been proposed. Such an apparatus has a channel-formed plate-shaped member comprised of two glass substrates joined together (see, for example, Japanese Laid-open Patent Publication (Kokai) No. 8-178897).

Since it is necessary to make the sample solution flow while maintaining the liquid characteristics thereof, the channel formed in the plate-shaped member used in such an apparatus usually has a depth of approximately 50 to 100 μm. If photothermal conversion spectroscopic analysis is carried out with the solution that is the target of measurement flowing through such a channel, then the thickness (depth) of the target of measurement will be much greater than the confocal length of the exciting light. For example, the confocal length in the case of converging exciting light of wavelength 532 nm using an objective lens of NA (numerical aperture) 0.4 is 3.9 μm, but the thickness of the channel is more than 10 times as large as the confocal length. Comparing such a case in which the thickness of the target of measurement is greater than the confocal length with the case of a thin film described above, the state will be as if a large number of thin films each having a thermal lens formed therein are piled on top of one another in the thickness direction, and hence ultimately the effect will be the integral thereover; it is thus anticipated that the optimum value of the shift in the focal position between the exciting light and the detecting light will be larger than in the case of a thin film. However, if the shift in the focal position between the exciting light and the detecting light is too large, then the amount of the detecting light passing through the thermal lens produced by the exciting light will be too low, and hence the detection sensitivity will drop. Regarding the chromatic aberration possessed by the objective lens used in the photothermal conversion spectroscopic analysis method, the shift (ΔL) between the focal position of the exciting light and the focal position of the detecting light is thus preferably in a range of 2 to 30 times, more preferably 2 to 25 times, yet more preferably 3 to 25 times, the confocal length for the exciting light.

In the case, for example, that the intensity of the exciting light used in the photothermal conversion spectroscopic analysis method is low, or the concentration of the target of measurement is low, the power of the thermal lens at a place away from the focal position of the exciting light will be low, and hence it is anticipated that the thermal lens effect integrated over the whole thickness of the target of measurement will be low. In such a case, it is preferable to make ΔL lower than stated above. ΔL is thus preferably in a range of 2 to 25 times, more preferably 3 to 25 times, yet more preferably 3 to 20 times, the confocal length for the exciting light.

An example will now be given of how much chromatic aberration can be obtained using a gradient index rod lens. An SML lens as listed in the SELFOC lens catalog of Nippon Sheet Glass Co., Ltd. will be used as the gradient index rod lens. The lens characteristics at a diameter of 1.8 mm are listed in the catalog, and hence these will be used converted to characteristic values for a diameter of 1 mm.

In the case that the channel-formed plate-shaped member is made of Pyrex (registered trademark) glass, the thickness of the portion above the channel (i.e. the thickness of the upper glass 201) is 0.18 mm, the depth of the channel is 0.1 mm, the diameter of the SML gradient index rod lens is 1 mm, the effective diameter for light actually passing through the lens is 0.7 mm, the rod length is 1.7 mm, the wavelength of the exciting light is 488 nm, the wavelength of the detecting light is 633 nm, and the focal position of the exciting light is made to be in the very middle of the channel, the shift (ΔL) in the focal position between the exciting light and the detecting light is 45 μm. The NA at the focal position in this case is 0.46, and hence the confocal length for the exciting light is 2.7 μm. ΔL is thus approximately 17 times the confocal length.

Figure 2:
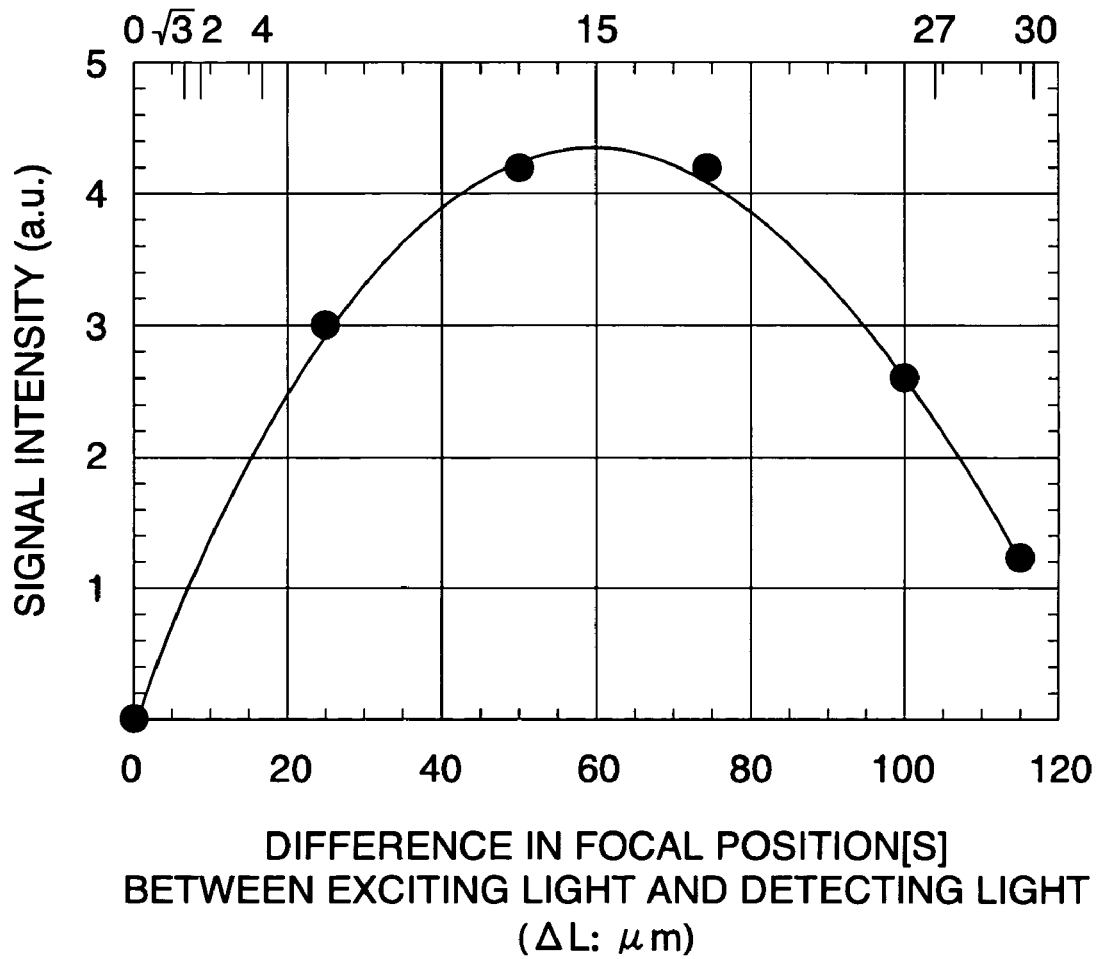
FIG. 2 is a graph showing an example of the relationship between ΔL and signal intensity in the photothermal conversion spectroscopic analysis method.
Figure 3:
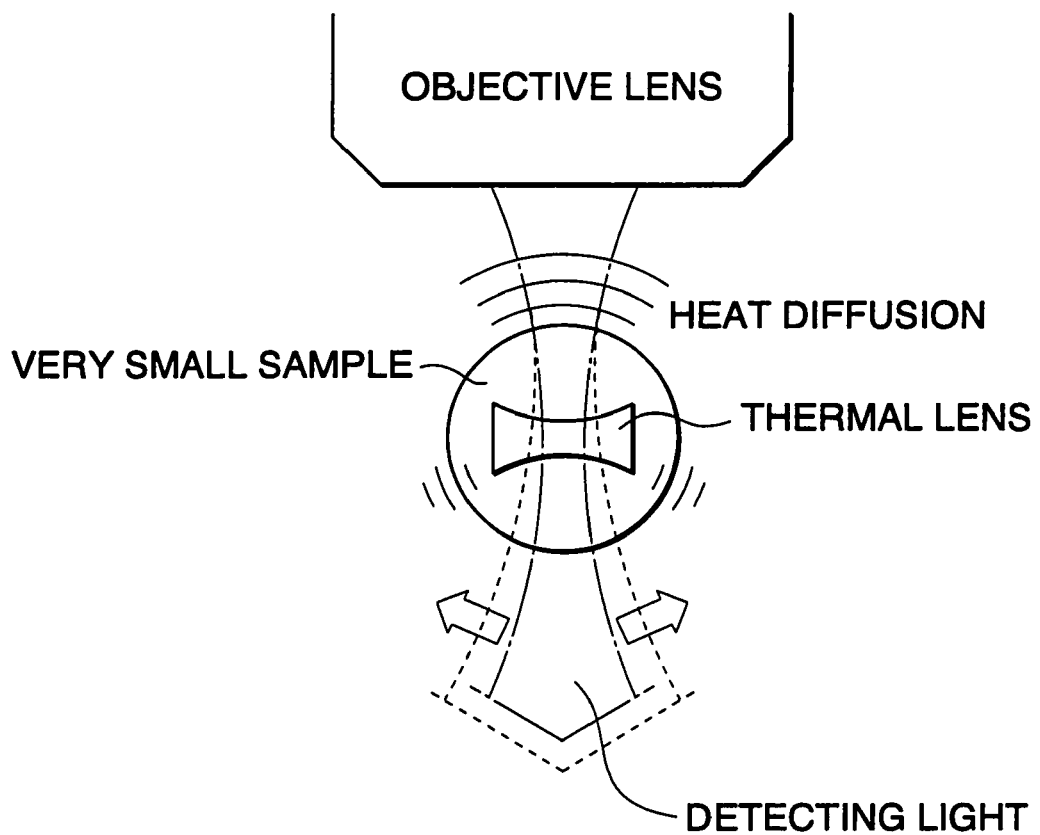
FIG. 3 is a view useful in explaining the principle of a thermal lens.
Figure 4A:
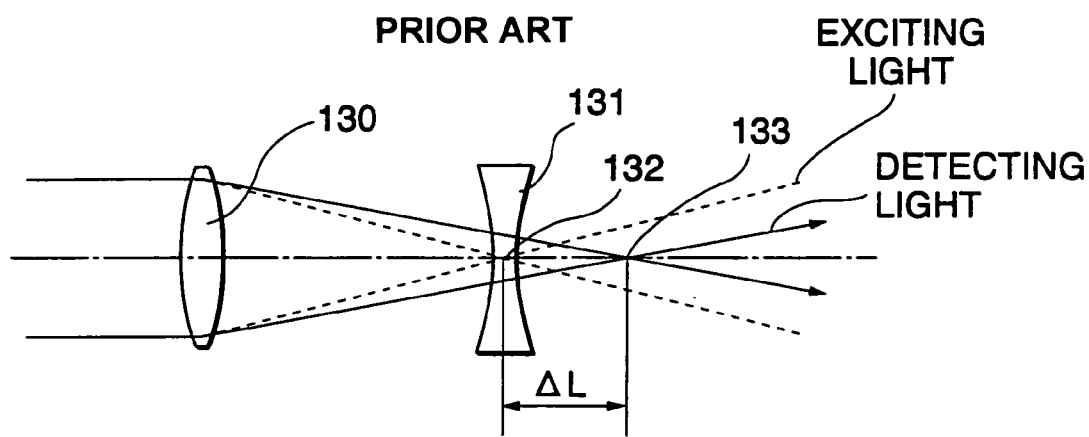
FIG. 4A is a view useful in explaining the formation position of a thermal lens and the focal position of detecting light in the direction of travel of exciting light, and shows a case in which an objective lens has chromatic aberration.
Figure 4B:
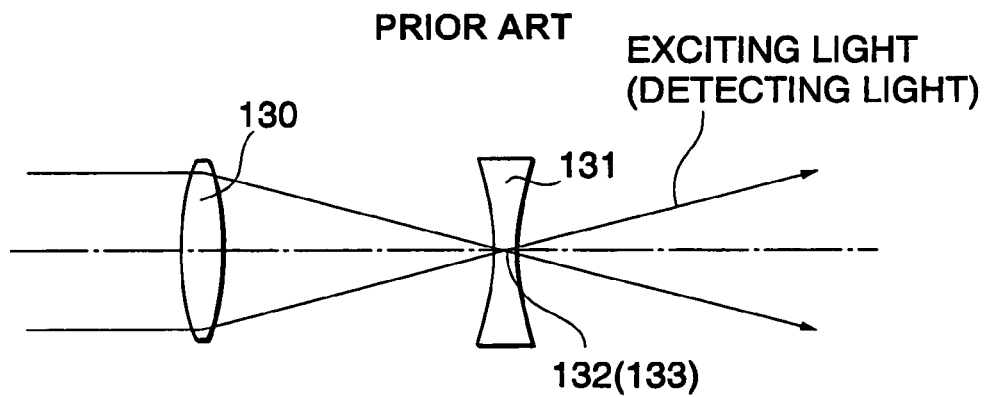
FIG. 4B is a view useful in explaining the formation position of the thermal lens and the focal position of the detecting light in the direction of travel of the exciting light, and shows a case in which the objective lens does not have chromatic aberration.
Figure 5A:
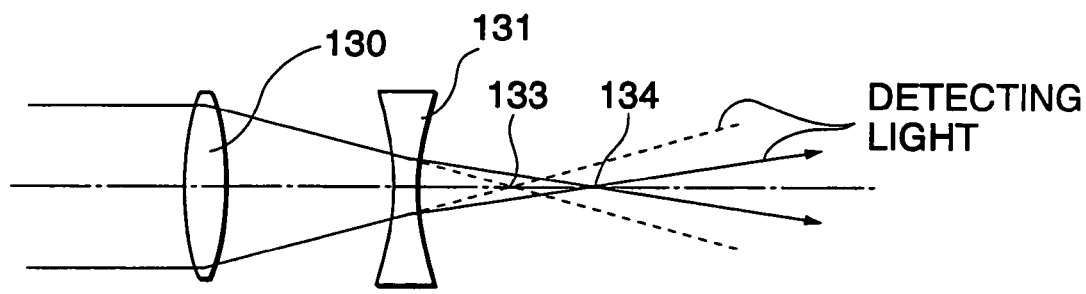
FIG. 5A is a view useful in explaining the formation position of the thermal lens and the focal position of the detecting light in the direction of travel of the exciting light, and shows a case in which the thermal lens is formed on the objective lens side relative to the focal position of the detecting light.
Figure 5B:
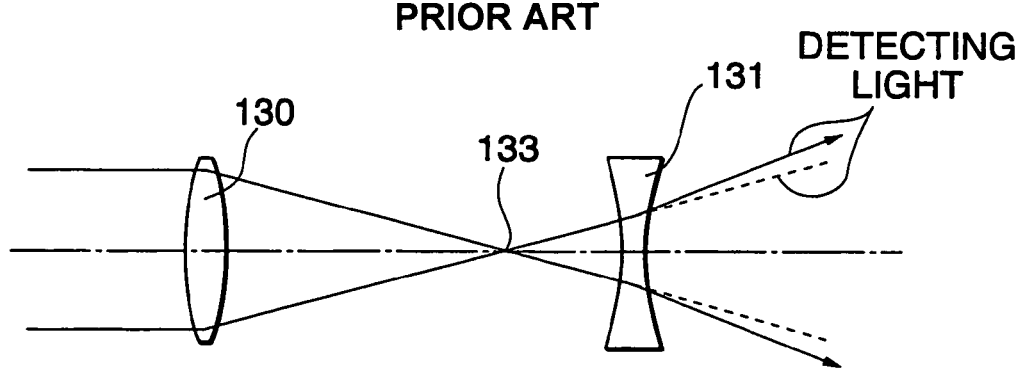
FIG. 5B is a view useful in explaining the formation position of the thermal lens and the focal position of the detecting light in the direction of travel of the exciting light, and shows a case in which the thermal lens is formed on the opposite side to the objective lens relative to the focal position of the detecting light.
Figure 6:
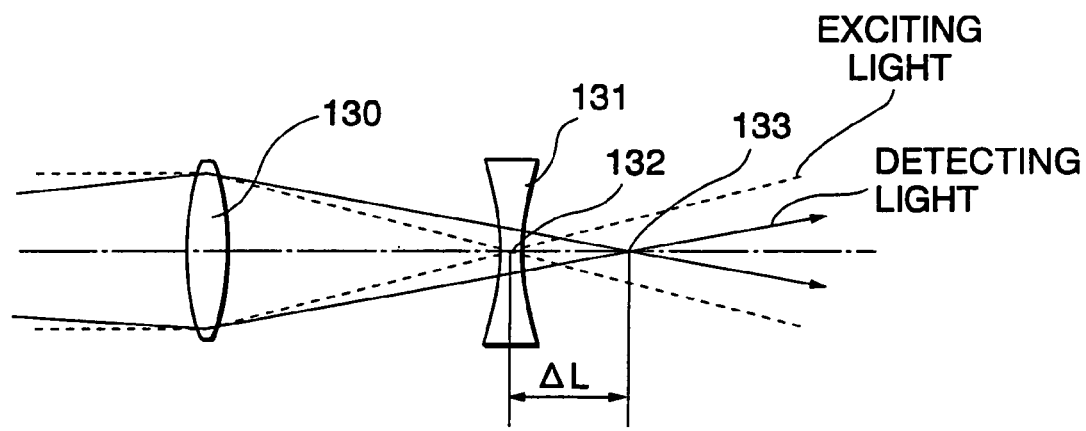
FIG. 6 is a view useful in explaining a method of detecting changes in refractive index of a thermal lens in a conventional photothermal conversion spectroscopic analysis apparatus.

FIG. 2 is a graph showing an example of the relationship between ΔL and the signal intensity in the photothermal conversion spectroscopic analysis method. The signal intensity shown in FIG. 2 was measured under the following conditions.

A microscope objective lens having no chromatic aberration and an NA of 0.4 was used as an objective lens. The exciting light was led to the objective lens as it is, and the detecting light was diverged or converged before being introduced into the objective lens, thus changing the focal position of the detecting light. The sample was an aqueous solution of Sunset Yellow of concentration $10^{-4}$M, and this was put into a channel of thickness 0.1 mm. The wavelength of the exciting light was 532 nm, and the wavelength of the detecting light was 633 nm. Under these conditions, the focal position of the exciting light was made to be in the center of the channel, and the signal intensity obtained using the photothermal conversion spectroscopic analysis method was measured while shifting the focal position of the detecting light from the center of the channel along the optical axis; FIG. 2 shows a plot of the results obtained.

According to FIG. 2, the signal intensity is highest when ΔL is approximately 60 μm, which is approximately 15 times the confocal length for the exciting light (the confocal length for the exciting light was 3.9 μm). The range of ΔL over which the signal intensity obtained was at least half of the maximum intensity is from 4 times to 27 times the confocal length for the exciting light.

A wavelength filter 116 that separates the exciting light and the detecting light and selectively transmits only the detecting light, and a photoelectric converter 117 that detects the detecting light that has been transmitted by the wavelength filter 116, are disposed at a location facing the rod lens 10 with the channel-formed plate-shaped member 20 therebetween, this being a location facing onto the channel 204 of the channel-formed plate-shaped member 20. A pinhole may be inserted in front of the photoelectric converter 117 so that only part of the detecting light is transmitted. The signal obtained by the photoelectric converter 117 is amplified by a pre-amplifier 121, and is then sent to a lock-in amplifier 122 where the signal is synchronized with the chopper 112, before being analyzed by a computer 123.

According to the present embodiment, the rod lens 10 has an amount of chromatic aberration suited to the wavelengths of the exciting light and detecting light used, and the dimensions of the channel 204 of the channel-formed plate-shaped member 20 used in the measurement; measurement can thus be carried out with high sensitivity, and moreover it is not necessary to externally provide an optical system for adjusting the focal positions of the exciting light and the detecting light, and hence the apparatus can be made smaller in size.

INDUSTRIAL APPLICABILITY

As described in detail above, according to the present invention, the exciting light and the detecting light have different frequencies to one another, and the converging lens satisfies a condition that the length of the shift in the focal position of the detecting light from the focal position of the exciting light is in a range of 2 times to 30 times the confocal length at the frequency of the exciting light; as a result, sufficient signal intensity can be obtained, and hence measurement can be carried out with high sensitivity.

In the present invention, the exciting light and the detecting light have different frequencies to one another, and the converging lens satisfies a condition that the length of the shift in the focal position of the detecting light from the focal position of the exciting light is in a range of 2 times to 25 times the confocal length at the frequency of the exciting light; as a result, the signal intensity is yet higher, and hence measurement can be carried out with yet higher sensitivity.

In the present invention, the converging lens is a rod lens; as a result, an optical system for adjusting the focal positions of the exciting light and the detecting light can be omitted, and hence the apparatus can be made smaller in size.

What is claimed is:

1. A photothermal conversion spectroscopic analysis method comprising:
   convergently irradiating exciting light and detecting light onto a sample through a same converging lens such that the convergent irradiation of the exciting light produces a thermal lens in the sample; and
   measuring a change in intensity accompanying deflection of the detecting light upon passing through the thermal lens;
   wherein the convergently irradiated exciting light and detecting light have respective different frequencies; and
   wherein the converging lens satisfies a condition that a length of a shift in a focal position of the detecting light from a focal position of the exciting light is in a range of 2 times to 30 times a confocal length at the frequency of the exciting light.

2. A photothermal conversion spectroscopic analysis method as claimed in claim 1, wherein the converging lens comprises a rod lens.

3. A photothermal conversion spectroscopic analysis method comprising:
   convergently irradiating exciting light and detecting light onto a sample through a same converging lens such that the convergent irradiation of the exciting light produces a thermal lens in the sample; and
   measuring a change in intensity accompanying deflection of the detecting light upon passing through the thermal lens;
   wherein the convergently irradiated exciting light and detecting light have respective different frequencies; and
   wherein the converging lens satisfies a condition that a length of a shift in a focal position of the detecting light from a focal position of the exciting light is in a range of 2 times to 25 times a confocal length at the frequency of the exciting light.

4. A photothermal conversion spectroscopic analysis method as claimed in claim 3, wherein the converging lens comprises a rod lens.

5. A photothermal conversion spectroscopic analysis apparatus comprising:
   a converging lens for convergently irradiating both exciting light and detecting light onto a sample such that the convergent irradiation of the exciting light produces a thermal lens in the sample; and
   measurement means for measuring a change in intensity accompanying deflection of the detecting light upon passing through the thermal lens;
   wherein the convergently irradiated exciting light and detecting light have respective different frequencies; and
   wherein said converging lens satisfies a condition that a length of a shift in a focal position of the detecting light from a focal position of the exciting light is in a range of 2 times to 30 times a confocal length at the frequency of the exciting light.

6. A photothermal conversion spectroscopic analysis apparatus as claimed in claim 5, wherein said converging lens comprises a rod lens.

7. A photothermal conversion spectroscopic analysis apparatus comprising:
   a converging lens for convergently irradiating both exciting light and detecting light onto a sample such that the convergent irradiation of the exciting light produces a thermal lens in the sample; and
   measurement means for measuring a change in intensity accompanying deflection of the detecting light upon passing through the thermal lens;
   wherein the convergently irradiated exciting light and detecting light have respective different frequencies; and
   wherein said converging lens satisfies a condition that a length of a shift in a focal position of the detecting light from a focal position of the exciting light is in a range of 2 times to 25 times a confocal length at the frequency of the exciting light.

8. A photothermal conversion spectroscopic analysis apparatus as claimed in claim 7, wherein said converging lens comprises a rod lens.

* * * * *